United States Patent [19]

Ichikawa et al.

[11] 4,153,630
[45] May 8, 1979

[54] INCLUSION COMPOUNDS, PROCESS FOR PREPARATION THEREOF, AND PROCESS FOR SEPARATING ISOMERS USING THE INCLUSION COMPOUNDS

[75] Inventors: Yataro Ichikawa, Fuchu; Yoshiyuki Yamanaka, Iwakuni; Hideki Tsuruta, Hino; Mamoru Yamamoto; Kenichi Kato, both of Iwakuni, all of Japan

[73] Assignee: Teijin Limited, Osaka, Japan

[21] Appl. No.: 735,549

[22] Filed: Oct. 26, 1976

[30] Foreign Application Priority Data

Oct. 22, 1975 [JP] Japan .................................. 50/126259
May 26, 1976 [JP] Japan .................................. 51/59930
May 26, 1976 [JP] Japan .................................. 51/59931

[51] Int. Cl.$^2$ .............................................. C07C 7/00
[52] U.S. Cl. ..................... 260/578; 260/582; 260/645; 260/650 R; 260/651 R; 260/674 SE; 260/674 WC; 568/750; 568/751; 568/752; 585/25; 585/409; 585/422; 585/817; 585/840; 585/867
[58] Field of Search ..... 260/668 R, 674 SE, 674 WC, 260/582, 645, 650 R, 651 R, 578; 568/750, 751, 752

[56] References Cited

U.S. PATENT DOCUMENTS 3,426,068  2/1969  Coscia ........................ 260/674 WC

FOREIGN PATENT DOCUMENTS 0872819  7/1961  United Kingdom ............ 260/674 WC

OTHER PUBLICATIONS

"Clathration of Hard-to-Separate Aromatic Mixtures with New Werner Complexes", by Radzitzky et al., I&EC Process Design and Development, vol. 1, No. 1, (Jan. 1962), pp. 10-14.

*Primary Examiner*—O. R. Vertiz
*Assistant Examiner*—Wayne A. Langel
*Attorney, Agent, or Firm*—Sherman & Shalloway

[57] ABSTRACT

An inclusion compound comprising meta-cyclophane of the formula

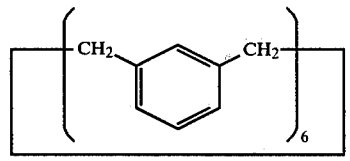

and at least one benzene derivative included therein. And a process for separating an isomer containing a substituent at least at the 1- and 4-positions from a mixture containing isomers of a benzene derivative, which comprises contacting the meta-cyclophane with the mixture containing isomers of a benzene derivative thereby to form an inclusion compound in which an isomer containing a substituent at least at the 1- and 4-positions is included in the meta-cyclophane, then separating the inclusion compound from the mixture, and thereafter separating the isomer from the inclusion compound.

13 Claims, No Drawings

INCLUSION COMPOUNDS, PROCESS FOR PREPARATION THEREOF, AND PROCESS FOR SEPARATING ISOMERS USING THE INCLUSION COMPOUNDS

This invention relates to an inclusion compound containing meta-cyclophane as a host and a benzene derivative as a guest, a process for its preparation, and a process for its utilization. More specfically, the invention relates to a process for separating a specified isomer from an isomeric mixture containing a benzene derivative utilizing the inclusion compound.

p-Xylene is a very important raw material for polyesters, and as well known, is prepared by separation and purification from mixed xylene (a mixture of p-, o- and m-isomers). However, as these isomers have very close boiling points from each other, it is extremely difficult to separate the mixture into the individual isomers by a conventional separating procedure such as distillation or crystallization. The same can be said with respect to other benzene derivatives. This will be clearly seen from the following tabulation of the boiling points (° C. at normal atmospheric pressure) of isomers of various benzene derivatives.

| Disubstituted benzene derivatives | o-Isomer | m-Isomer | p-Isomer |
| --- | --- | --- | --- |
| Xylene | 144.4 | 139.1 | 138.3 |
| Ethyltoluene | 165.1 | 161.3 | 162.0 |
| Cresol | 190.8 | 202.8 | 201.8 |
| Dichlorobenzene | 180.4 | 173.0 | 174.6 |
| Chlorophenol | 174.5 | 214.0 | 220.0 |
| Chloroaniline | 208.8 | 228.5 | 230.5 |
| Bromotoluene | 181.8 | 183.7 | 184.5 |
| Chlorotoluene | 159.3 | 162.3 | 162.3 |
| Toluidine | 199.7 | 203.3 | 200.4 |
| Chloroethylbenzene | 177.6 | 181.1 | 184.3 |
| Ethylanisole | 187.1 | 196.5 | 196.5 |
| Isopropyl phenol | 214.5 | 228.0 | 228.2 |
| Diethylbenzene | 183.5 | 181.1 | 183.8 |
| Cymene | 178.3 | 174.9 | 177.1 |

| Trisubstituted benzene derivative | 1,2,3-Isomer | 1,2,4-Isomer | 1,3,5-Isoer |
| --- | --- | --- | --- |
| Trimethylbenzene | 176.1 | 169.2 | 164.7 |

Various methods have been suggested heretofore to separate these isomers utilizing inclusion compounds. For example, for the separation of p-xylene from mixed xylene, American Chemical Society, 3747 (1952) and 2339 (1958) discloses a method which utilizes an inclusion compound based on tri-o-thymotide; U.S. Pat. No. 3,456,028, a method utilizing an inclusion compound based on α-cyclodextrin; and Japanese Patent Publication No. 5155/62, a method utilizing an inclusion compound based on natural or synthetic zeolite. The compound containing α-cyclodextrin as a host is utilized, for example, to separate diethylbenzene isomers (Japanese Laid-Open Patent Publication No. 151,826/75), trimethylbenzene isomers (Japanese Laid-Open Patent Publication No. 96,530/75), and alkyltoluene isomers (Japanese Laid-Open Patent Publication No. 100,217/75).

These known methods, however, have some defects or other, and are not entirely satisfactory. For example, all of these methods suffer from poor selectivity.

In the case of separating p-xylene from mixed xylene, the degree of selection $\beta(p^x/m^x)$ to be defined hereinbelow is about 3 to 9 at most. Or α-cyclodextrin is expensive.

It is an object of this invention therefore to provide a process for separating isomers of a benzene derivative at high selection degrees and low costs as a result of discovering a novel inclusion compound.

Other objects of this invention will become apparent from the following description.

The present inventors have found that when meta-cyclophane of the following formula

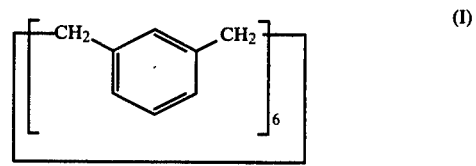

(I)

is contacted with at least one benzene derivative, an inclusion compound containing the meta-cyclophane as a host and the benzene derivative as a guest can be formed. More specifically, they have found that when meta-cyclophane of the following formula

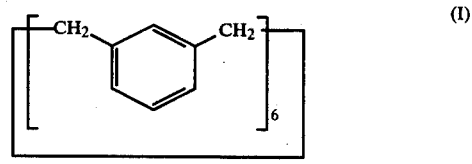

(I)

is contacted with a mixture containing isomers of a benzene derivative of the following formula

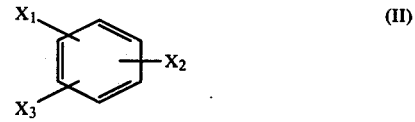

(II)

wherein $X_1$, $X_2$ and $X_3$ are defined by (a), (b), or (c) below:

(a) $X_1$ and $X_2$ represent a hydrogen atom, and $X_3$ represents —$CH_3$, —$C_2H_5$, —$C_3H_7$, —COOH, —$COOCH_3$, —$COOC_2H_5$, —OH, —OR(wherein R is an alkyl group containing 1 to 4 carbon atoms), —$NH_2$, —$NO_2$, or a halogen atom;

(b) $X_1$ represents a hydrogen atom, and $X_2$ and $X_3$, independently from each other, represent —$CH_3$, —$C_2H_5$, —$C_3H_7$, —$COOCH_3$, —OH, —$OCH_3$, —$NH_2$, —$NO_2$ or a halogen atom; and (c) all of $X_1$, $X_2$ and $X_3$ represent —$CH_3$, —$C_2H_5$, or a halogen atom;

an inclusion compound can be obtained in which an isomer having a substituent at least at the 1- and 4-positions (that is, a p-isomer when the benzene derivative is a disubstituted derivative, and a 1,2,4-isomer when it is a trisubstituted derivative) is included in the meta-cyclophane.

Thus, according to the present invention, there is provided a process for separating an isomer having a substituent at least at the 1- and 4-positions from a mixture containing isomers of a benzene derivative, which comprises contacting meta-cyclophane of the following formula

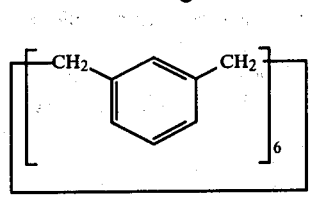

with a mixture containing isomers of a benzene derivative of the following formula

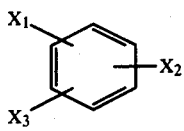

wherein $X_1$, $X_2$ and $X_3$ are the same as defined above, thereby to form an inclusion compound in which the meta-cyclophane includes the isomer having a substituent at least at the 1- and 4-positions, then separating the inclusion compound from the mixture, and thereafter separating the isomer from the inclusion compound.

The m-cyclophane of formula (I) can be prepared by various methods among which are:

(a) the method disclosed in Helvetica Chimica Acta, Vol. 50, $F_2$ sciculus 7 (1967) No. 204;

(b) the method disclosed in Synthesis 424 (1974); and (c) the method disclosed by the present inventors in Japan which comprises dimerization-cyclization of bis(m-phenetile)-m-chloromethyl benzene of the following formula

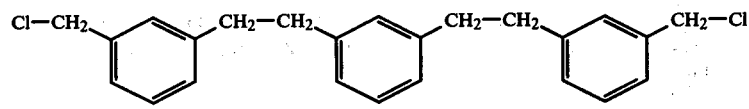

in the presence of, for example, an alkali metal.

Various methods can be employed to obtain the inclusion compound of the meta-cyclophane of formula (I) and the benzene derivative of formula (II) in the present invention. For example, the meta-cyclophane is added to the benzene derivative mixture, and the resulting crystals are separated. Or in order to perform the inclusion to a greater extent, the meta-cyclophane is added to the benzene derivative mixture, and the resulting mixture is heated to form a complete solution, after which the solution is cooled, and the resulting crystals are separated.

Preferred examples of the benzene derivative mixture from which an isomer can be separated by the process of this invention are listed below.

(1) Mixed xylene containing p-xylene (2) Diethylbenzene-containing mixture obtained by ethylating ethylbenzene (3) Chloro-ethyl(or methyl)benzene-containing mixture obtained by chlorinating ethyl(or methyl) benzene (4) Methyl or ethyl phenol-containing mixture obtained by methylation or ethylation of phenol (5) Mixture containing methyl or ethylphenol obtained by oxidizing an alkylbenzene or from coal tar (6) Ethyltoluene- or nitrotoluene-containing mixture obtained by ethylation or nitration of toluene (7) Trimethylbenzene-containing mixture such as $C_9$ fraction or coal tar According to the process of this invention, an inclusion compound can be obtained even when the content of an isomer to be separated in the mixture is very low.

Hence, the invention finds a very wide range of application, and can is used, for example, not only for increasing the purity of an isomer to be separated, but also for removing a benzene derivative from a mixture containing the benzene derivative as an impurity in a very small amount. Ingredients other than the benzene derivative may be contained in the benzene derivative mixture unless the other ingredients impede the including action of the meta-cyclophane or cause the benzene derivative isomer to drop off from the inclusion compound obtained. Preferably, however, compounds which readily dissolve the inclusion compound should not be contained in the mixture.

The proportion of the meta-cyclophane (I) used in the process of this invention is 0.01 to 50 moles, preferably 0.05 to 5 moles, especially preferably 0.1 to 2 moles, per mole of the benzene derivative isomer to be separated. With decreasing proportion of the meta-cyclophane, the degree of selection increases.

The contacting of the meta-cyclophane (I) with the benzene derivative mixture is carried out generally at a temperature of $-50°$ to 350° C., preferably 0° to 200° C., especially 20° to 150° C. Where the mixture is a solid, it is contacted in the form of a solution in a suitable solvent.

Preferably, the feeding of the materials is performed such that the slurry concentration of the resulting inclusion compound becomes 1 to 60% by weight, particularly 10 to 40% by weight.

In order to separate the resulting inclusion compound from the slurry containing it, it is preferred to use a solid-liquid separation technique (e.g., filtration, centrifugal separation, or precipitation), or a method comprising evaporating off the solvent. Irrespective of the type of the separating procedure used, the operating temperature is $-50°$ to 120° C., preferably 0° to 90° C.

In the inclusion compound obtained in this invention, the amount of the benzene derivative included in the meta-cyclophane differs according to the type of the benzene derivative, but is usually 0.1 to 1.5 moles, frequently 0.5 to 1.0 mole, per mole of the meta-cyclophane (I).

The benzene derivative isomer included in the resulting inclusion compound based on meta-cyclophane (I) can be separated by various methods among which are:

(a) a method which comprises heating the inclusion compound to 90° to 400° C., preferably 120° to 300° C. thereby to evaporate off the benzene derivative isomer included in it; and (b) a method which comprises contacting the inclusion compound with a solvent which cna be more easily included by the meta-cyclophane (I) than the benzene derivative isomer included in it (e.g., benzene, cyclohexane or toluene) to replace the isomer by the solvent, separating the inclusion compound comprising the meta-cyclophane and the solvent by filtration, and then separating the isomer from the filtrate by evaporation.

The following Examples illustrate the present invention more specifically.

MC used in these Examples represents the meta-cyclophane of formula (I). All parts are by weight unless otherwise specified. The degree of selection $\beta(A/B)$ is a value calculated in accordance with the following equation.

$$\beta(A/B) = \frac{C_A/C_B \text{ in the inclusion compound}}{C_A/C_B \text{ in the liquid left after the separation of the inclusion compound}}$$

wherein $C_A$ represents the moles of component A in the benzene derivative mixture, and $C_B$, the moles of component B in the mixture.

The inclusion ratio is the molar ratio of the guest in an inclusion compound to the host [meta-cyclophane of formula (I)].

EXAMPLE 1

2.0 Parts of MC was added to 16 parts of a mixture consisting of 10 parts of methanol and 1.5 parts each of p-xylene (pX), m-xylene (mX), o-xylene (oX) and ethylbenzene (EB). The mixture was heated to 100° C. to form a complete solution. The solution was cooled to 50° C. to form acicular crystals.

The mixture was filtered at 50° C., and the resulting cake was dried at room temperature and 100 mm Hg abs. for 1 hour. The adhering xylene and methanol were removed to afford 2.2 parts of an inclusion compound as white acicular crystals. A gas-chromatographic analysis of a part of the crystals showed that the inclusion somppound scarcely contained methanol. The degrees of selection calculated from the analytical values of the xylenes were as follows:

$\beta(pX/mX)=30, \beta(pX/oX)=50,$ and $\beta(pX/EB)=160$.

The concentration of pX in the guest [pX/(pX+mX+oX+EB] was 94 mole%.

The crystals were subjected to an infrared spectrum analysis, and the results were as follows:
MC: 3050-2850, 1610, 1590, 1490, 1455, 1080, 890, 790, 700, 460 (cm$^{-1}$). p-Xylene: 3050-2850, 1515, 790, 485 (cm$^{-1}$). Inclusion compound: 3050-2850, 1610, 1590, 1515, 1490, 1453, 1080, 890, 790, 700, 485, 460 (cm$^{-1}$).

Then, 0.0083 part of the resulting crystals were analyzed by a differential thermal balance, and a weight decrease of 0.0012 part was observed at 90° to 115° C. From the weight decrease, an inclusion ratio [(pX+mX+oX+EB)/MC (mole/mole)] of 0.99 as obtained.

The guest was separated by evaporating 2.0 parts of the resulting crystals at 250° C. and 300 mm Hg abs. to afford 0.22 part of p-xylene having the same composition as described hereinabove ($pX$=94 mole%).

EXAMPLES 2 to 4

0.1 Part of MC was added to a mixture of 1.0 part of each of the solvents indicated in the following table and 1.0 part of p-xyelene, and the mixture was heated at 70 to 130° C. The solution was cooled to room temperature to form crystals. The crystals were separated from the solution by suction filtration at room temperature, and then dried at room temperature and 0.3 mm Hg abs. for 1 hour. The resulting white crystals (inclusion compound) were dissolved in another solvent, and gas-chromatographically analyzed. The degrees of selection [$\beta(pX/\text{solvent})$] were calculated, and the results are tabulated below.

| Example | Solvent | $\beta(pX/\text{solvent})$ |
|---|---|---|
| 2 | methanol | $\sim \infty$ |
| 3 | nitrobenzene | 89 |
| 4 | N,N-dimethyl formamide | 35 |

EXAMPLE 5

1.0 Part of benzene was added to 0.2 part of an inclusion compound as white acicular crystals [composition: $(pX+mX+oX+EB)/MC=0.88$ (mole/mole), $pX/(pX+mX+oX+EB)=0.90$ (mole/mole)] obtained in the same way as in Example 1. The mixture was fed into a sealed tube, and heated to 130° C. to dissolve the crystals completely. The solution was cooled to room temperature to form acicular crystals again. The mixture was filtered to separate the cake. The total amount of the residue and the wash liquid resulting after washing the cake with 0.5 part of benzene (to be referred to as the filtrate) was 1.1 parts.

The filtrate was gas-chromatographically analyzed, and it was found that the ratio of (pX+mX+oX+EB)/benzene was 2.1 by weight, and the molar ratio of pX/(pX+mX+oX+EB) was 0.90. Then, benzene was evaporated off from the filtrate to obtain p-xylene containing 10% of impurities (mX+oX+EB) at a recovery ratio of 80%

EXAMPLE 6

0.2 Parts of MC was added to 1.5 parts of a mixture consisting of 0.5 part each of p-diethylbenzene (pDEB), m-diethylbenzene (mDEB) and o-diethylbenzene (oDEB). The mixture was heated at 100° C. to form a complete solution. The solution was cooled to rrom temperature to form acicular crystals. The mixture was filtered, and the resulting crystals were dried at room temperature and 10 mm Hg abs. for about 30 minutes. The adhering diethylbenzene was removed to afford 0.22 part of an inclusion compound as white acicular crystals. The crystals was gas-chromatographically analyzed. The degrees of selection were as folows:

$\beta(pDEB/mDEB)=2.6,$ and $\beta(pDEB/oDEB)=32$.

The concentration of the pDEB in the guest is 0.75 (pDEB/(pDEB+mDEB+oDEB)]. The concentration of pDEB was thus found to be 2.3 times that in the diethylbenzene solution before contacting. The results of infrared spectrum analysis of these crystals were as follows:

MC: same as in Example 1 p-Diethylbenzene: 3050-2850, 1515, 1455, 830 (cm$^{-1}$). Inclusion compound: 3050-2850, 1610, 1590, 1515, 1490, 1453, 1080, 890, 830, 790, 700, 460 cm$^{-1}$.

Then, 0.010 part of the white acicular crystals were analyzed by a differential thermal balance, and a weight decrease of 0.0016 part was observed at 100° to 180° C. From the decrease, an inclusion ratio (molar ratio of diethylbenzene/MC) of 0.91 was obtained. The guest was separated fro 0.2 part of the resulting crystals by evaporation at 250° C. and 100 mm Hg abs. to afford 0.028 part of p-diethylbenzene having the same composition as set forth above (p-DEB=75 mole%).

EXAMPLE 7

0.2 Part of MC was added to 1.5 parts of a mixture consisting of 0.5 part each of pseudocumene (PC), mesitylene (MS), and hemimellitene (HM). The mixture was heated to 100° C. to form a complete solution. The solution was cooled to room temperature to form acicular crystals. The mixture was filtered, and the resulting crystals were dried at room temperature and B 10 mm Hg abs. for 1 hour. The adhering trimethylbenzenes were removed to afford 0.19 part of an inclusion compound as white acicular crystals. A part of the crystals was gas-chromatographically analyzed. It was found that the degrees of selection was as follows:

$\beta(PC/MS) = 150, \beta(PC/HM) = 22.$

The concentration of pseudocumene in the guest was 0.95 [PC/(PC+MS+HM)], and it was found that pseudocumene was concentrated markedly in the resulting crystals. The crystals were analyzed by infrared spectra, and the following results were obtained.

MC: same as in Example 1 Pseudocumene: 3200–2850, 1610, 1510, 1450, 1380, 800, 540, 440 (cm$^{-1}$). Inclusion compound: 3050–2850, 1610, 1590, 1490, 1455, 1080, 890, 800, 790, 700, 460 (cm$^{-1}$).

An absorption based on MC and an absorption based on PC (at 800 cm$^{-1}$) were observed, but no absorption ascribable to MS and HM was found.

From these results, it is assumed that these crystals were an inclusion compound with hardly any trimethylbenzenes adhering thereto but containing pseudocumene in a high concentration.

Then, 0.010 part of these white acicular crystals were analyzed by a differential thermal balance, and a weight decrease of 0.0015 part was observed at 100° to 170° C. From the weight decrease, an inclusion ratio (the mole ratio of PC/MC) of 0.89 was obtained.

The guest was separated from 0.15 part of the resulting crystals by evaporation at 300° C. and 100 mm Hg abs. to afford 0.02 part of pseudocumene having the same composition as set forth above (PC=95 mole%).

EXAMPLE 8

0.2 Part of MC was added to 1.0 part of a mixed solution consisting of 0.5 part each of p-nitrotoluene (pNT) and m-nitrotoluene (mNT). The mixture was heated to 120° C. to form a complete solution. The solution was cooled to about 40° C. to form acicular crystals. The mixture was filtered at about 40° C. The resulting crystals were washed with about 2 parts of methanol to remove the adhering nitrotoluenes to afford 0.23 part of an inclusion compound as white acicular crystals. Th crystals were gas-chromatographically analyzed, and it was found that they scarcely contained methanol but consisted substantially of p-nitrotoluene and m-nitrotoluene [$pNT/(pNT+mNT) = 97$ mole/mole]. Thus, the ratio of pNT/mNT in the feed was increased to about 34 times in the inclusion compound. From the results of the gas chromatographic analysis, the inclusion ratio (the mole ratio of (pNT+mNT)/MC) was 0.95, and the degree of selection $\beta(pNT/mNT)$ was 34. The crystals were analyzed by infrared spectra, and the following results were obtained. Absorptions ascribable to MC and pNT were observed, but no other absorption was seen.

MC: same as in Example 1. pNT: 1600, 1520, 1350, 1110, 860, 840, 785, 735, 680 (cm$^{-1}$). Inclusion compound: 3050–2850, 1610, 1590, 1490, 1455, 1350, 1080, 890, 860, 790, 700, 460 (cm$^{-1}$).

0.22 Parts of the resulting inclusion compound was treated in the same manner as in Example 5 to afford 0.035 part of p-nitrotoluene containing about 3% of impurities (m- and o-nitrotoluenes).

EXAMPLE 9

0.2 Part of MC was added to 1.5 parts of a mixed solution consisting of 0.5 part each of p-toluidine (pTD), m-toluidine (mTD) and o-toluidine (oTD). The mixture was heated to 120° C. to form a complete solution. The solution was cooled to about 40° C. to form acicular crystals. The mixture was filtered at about 40° C., and the resulting crystals were washed with about 2 parts of methanol to remove the adhering toluidines, followed by vacuum drying at 40° C. and about 50 mm Hg abs. for 10 minutes to afford 0.22 part of an inclusion compound as white acicular crystals. The crystals were gas-chromatographically analyzed, and it was found that they scarcely contained methanol, but consisted substantially of p-toluidine, m-toluidine and o-toluidine. The ratio of pTD/(pTD+mTD+oTD) was 0.67. From the results of the gas chromatographic analysis, the inclusion ratio [(pTD+mTD+oTD)/MC molar ratio] was 0.89, and the degrees of selection were $\beta(pTD/mTD) = 9$. and $\beta(pTD/oTD) = 2.6$. The guest was separated from 0.21 part of the resulting inclusion compound by evaporation at about 150 mm Hg and about 250° C. to afford 0.025 part of p-toluidine having the same composition as set forth above.

EXAMPLE 10

0.2 part of MC was added to 1.5 parts of a mixed solution consisting of 0.5 part each of p-cresol (pCS), m-cresol (mCS), and o-cresol (oCS). The mixture was heated to 120° C. to form a complete solution. The solution was cooled to about 40° C. to form acicular crystals. The mixture was filtered at about 40° C., and the resulting crystals were washed with about 2 parts of methanol to remove the adhering cresols. The crystals were than vacuum-dried at about 0.3 mm Hg abs. and 40° C. for about 10 minutes to afford 0.22 part of an inclusion compound as white acicular crystals. The crystals were gas-chromatographically analyzed, and it was found that they scarcely contained methanol, but consisted substantially only of p-cresol, m-cresol and o-cresol. The molar ratio of pCS/(pCS+mCS+oCS) was 0.70. From the results of the gas chromatographic analysis, it was found that the inclusion ratio [(pCS+mCS+oCS)/MC molar ratio) was 0.94, and the degrees of selection were $\beta(pCS/mCS) = 5.0$ and $\beta(pCS/oCS) = 4.5$.

0.21 Part of the resulting inclusion compound was heated at 250° C. and about 150 mm Hg abs. to evaporate off the guest and thereby to afford 0.025 part of p-cresol having the same composition as set forth above (purity about 70 mole%).

EXAMPLE 11

0.2 Part of MC was added to 1.5 parts of a mixed solution consisting of 0.5 part each of p-ethyltoluene (pET), m-ethyltoluene (mET) and o-ethyltoluene (oET). The mixture was heated to 120° C. to form a complete solution. The solution was cooled to 40° C. to form acicular crystals. The mixture was filtered at 40° C., and the resulting crystals were washed with about 2 parts of methanol to remove the adhering ethyltoluenes. The crystals were then vacuum-dried at 40° C. and about 50 mm Hg abs. for about 10 minutes to afford 0.23 part of an inclusion compound as white acicular crystals. The crystals were gas-chromatographically analyzed, and it was found that they scarcely contained methanol but consisted substantially only of p-ethyltoluene, m-ethyltoluene and o-ethyltoluene. The pET/(pET+mET+oET) molar ratio of 0.94. From the results of the gas-chromatographic analysis, it was found that the inclusion ratio (the molar ratio of (pET+mET+oET)/MC was 0.83, and the degrees of selection were $\beta(pET/mET)=20$, and $\beta(pET/oET)=150$.

The crystals were further analyzed by infrared spectra, and the following results were obtained. Absorptions ascribable to MC and pET were observed, but no other absorption was seen.

MC: same as in Example 1. p-Ethyltoluene: 2950, 1520, 1460, 815 $(cm^{-1})$. Inclusion compound: 3050–2850, 1610, 1590, 1490, 1455, 1080, 890, 815, 790, 700, 460 $(cm^{-1})$.

0.22 part of the resulting inclusion compound was heated at about 300 mm Hg abs. and 250° C. to separate the guest by evaporation to afford 0.027 part of p-ethyltoluene having the same composition as set forth above (purity of p-ethyltoluene 94 mole%).

EXAMPLE 12

0.2 Part of MC was added to 1.5 parts of a mixed solution consisting of 0.5 part each of p-ethylphenol (pEP), m-ethylphenol (mEP) and o-ethylphenol (oEP). The mixture was heated to 120° C. to form a complete solution. The solution was cooled to 40° C. to form acicular crystals. The mixture was filtered at 40° C., and the resulting crystals were washed with about 2 parts of methanol to remove the adhering ethylphenols, followed by vacuum-drying at 40° C. and about 50 mm Hg abs. for about 10 minutes to afford 0.22 of an inclusion compound as white acicular crystals. The crystals were gas-chromatographically analyzed, and it was found that they scarcely contained methanol, but consisted substantially only of p-ethylphenol, m-ethylphenol and o-ethylphenol. The molar ratio of pEP/(pEP+mEP+oEP) was 0.65. From the results of the gas-chromatographic anaylsis, it was found that the inclusion ratio [(pEP+mEP+oEP)/MC molar ratio) was 0.85, and the degrees of selection were $\beta(pEP/mEP)=3.5$, and $\beta(pEP/oEP)=4.5$.

0.21 Part of the resulting inclusion compound was treated in the same way as in Example 5 to afford 0.024 part of p-ethylphenol having the same composition as set forth above $[pEP/(pEP+mEP+oEP)=0.65$ mole/mole].

EXAMPLE 13

0.2 Part of MC was added to 1.0 part of a mixed solution consisting of 0.5 part each of p-isopropylphenol (pIPP) and o-isopropyphenol (oIPP). The mixture was heated to 120° C. to form a complete solution, and cooled to about 40° C. to form acicular crystals. The mixture was filtered at about 40° C., and the resulting crystals were washed with about 2 parts of methanol to remove the adhering isopropylphenols, followed by vacuum-drying at 40° C. and about 50 mm Hg abs. for about 10 minutes to afford 0.22 part of an inclusion compound as white acicular crystals. The crystals were gas-chromatrographically analyzed, and it was found that they scarcely contained methanol, but consisted substantially only of p-isopropylphenol and o-isopropylphenol. The pIPP/(pIPP+oIPP) molar ratio of 0.76. From the results of the gas-chromatographic analysis, it was found that the inclusion ratio [(pIPP+oIPP)/MC molar ratio] was 0.80, and the degree of selection $\beta(pIPP/oIPP)$ was 3.1.

0.21 Part of the resulting inclusion compound was treated in the same way as in Example 5 to afford 0.025 part of p-isopropylphenol having the same composition as set forth above $[pIPP/(pIPP+oIPP)=0.76]$.

EXAMPLE 14

0.2 Part of MC was added to 1.5 parts of a mixed solution consisting of 0.5 part each of p-dichlorobenzene (pDCB), m-dichlorobenzene (mDCB) and o-dichlorobenzene (oDCB). The mixture was heated to 120° C. to form a complete solution. The solution was cooled to about 40° C. to form acicular crystals. The mixture was filtered at about 40° C., and the resulting crystals were washed with about 2 parts of methanol to remove the adhering dichlorobenzenes, followed by vacuum-drying at about 40° C. and about 0.3 mm Hg abs. for about 10 minutes to afford 0.23 part of an inclusion compound as white acicular crystals. Th crystals were gas-chromatographically analyzed, and it was found tha they scarcely contained methanol, but consisted substantially only of p-dichlorobenzene, m-dichlorobenzene and o-dichlorobenzene. The pDCB/(pDCB+mDCB+oDCB) molar ratio was 0.67. From the results of the gas-chromatographic analysis, the inclusion ratio [(pDCB+mDCB+oDCB)/MC molar ratio] was 0.95, and the degrees of selection were $\beta(pDCB/mDCB)=6.5$ and $\beta(pDCB/oDCB)=3.0$.

0.22 Part of the resulting inclusion compound was heated at about 300 mm Hg abs. and 250° C. to separate the guest by evaporation to afford 0.037 part of p-dichlorobenzene having the same composition as set forth above.

EXAMPLE 15

0.2 Part of MC was added to 1.5 parts of a mixed solution consisting of 0.5 part each of p-chlorophenol (pCP), m-chlorophenol (mCP) and o-chlorophenol, (oCP). The mixture was heated to 120° C. to form a completely solution. The solution was cooled to about 40° C. to form acicular crystals. The mixture was filtered at about 40° C., and the resulting crystals were washed with about 2 parts of methanol to remove the adhering chlorophenols, followed by vacuum-drying at about 40° C. and about 0.3 mm Hg abs. for about 30 minutes to afford 0.22 part of an inclusion compound as white acicular crystals. The crystals were gas-chromatographically analyzed, and it was found that they scarcely contained methanol, but consisted substantially only of p-chlorophenol, m-chlorophenol and o-chlorophenol. The pCP/(pCP+mCP+oCP) molar ratio was 0.84. From the results of the gas-chromatrographic anaylsis, it was found that the inclusion ratio [(pCP+mCP+oCP)/MC molar ratio ] was 0.78, and the degrees of selection were $\beta(pCP/mCP)=11$ and $\beta(pCP/oCP)=10$.

0.21 Part of the resulting inclusion compound was treated in the same way as in Example 5 to afford 0.026 part of p-chlorophenol having the same composition was set forth above $[pCP/(pCP+mCP+oCP)=0.84]$.

EXAMPLE 16

0.2 Part of MC was added to 2.5 parts of a mixed solution consisting of 1.0 part of methanol and 0.5 part each of dimethyl terephthalate (DMT), dimethyl phthalate (DMP) and dimethyl isophthalate (DMI). The mixture was heated to 120° C. to form a complete solution. The solution was cooled to about 40° C. to form acicular crystals. The mixture was filtered at about 40° C., and the resulting crystals were washed with about 4 parts of methanol to remove the adhering dimethyl terephthalate, dimethyl phthalate and dimethyl isophthalate, followed by vacuum-drying at about 40° C. and about 50 mm Hg for about 30 minutes to afford 0.21 part of an inclusion compound as white acicular crystals. The crystals were analyzed gas-chromatographically, and it was found that they scarcely contained methanol, but consisted substantially only of dimethyl terephthalate, dimethyl phthalate, and dimethyl isophthalate. The DMT/(DMT+DMP+DMI) molar ratio of 0.61. From the results of the gas-chromatographic analysis, it was found that the inclusion ratio [(DMT+DMP+DMI)/MC molar ratio] was 0.81, and the degrees of selection were $\beta(DMT/DMP)=2.9$ and $\beta(DMT/DMI)=3.5$.

0.20 part of the resulting inclusion compound was treated in the same way as in Example 5 to afford 0.036 part of dimethyl isophthalate having the same composition as set forth above.

EXAMPLE 17

0.2 Part of MC was added to 2.5 parts of a mixed solution consisting of 1.0 part of methanol and 0.5 part each of p-dimethoxybenzene (pDMB), m-dimethoxybenzene (mDMB) and o-dimethoxybenzene (oDMB). The mixture was heated to 120° C. to form a complete solution. The solution was cooled to about 40° C. to form acicular crystals. The mixture was filtered at about 40° C., and the resulting crystals were washed with about 2 parts of methanol to remove the adhering dimethoxybenzenes, followed by vacuum-drying at about 40° C. and about 50 mm Hg abs. for about 30 minutes to afford 0.21 part of an inclusion compound as white acicular crystals. The crystals were gas-chromatographically analyzed, and it was found that they scarcely contained methanol, but consisted substantially only of p-dimethoxybenzene, m-dimethoxybenzene and o-dimethoxybenzene. The pDMB/(pDMB+mDMB+oDMB) molar ratio was 0.65. From the results of the gas-chromatographic analysis, it was found that the inclusion ratio [(pDMB+mDMB+oDMB)/MC molar ratio] was 0.85, and the degrees of selection were $\beta(pDMB/mDMB)=4.5$ and $\beta(pDMB/oDMB)=3.2$.

0.20 Part of the resulting inclusion compound was treated in the same way as in Example 5 to afford 0.027 part of p-dimethoxybenzene having the same composition as set forth above.

EXAMPLE 18

MC (6.0 parts) was added to 21.8 parts of a mixed solution consisting of 0.6 part of p-xylene (pX), 1.2 parts of m-xylene (mX) and 20 parts of methanol. The mixture was heated to 120° C. to form a complete solution. Cooling the solution to about 40° C. yielded acicular crystals. This mixture was filtered at about 40° C., and the resulting crystals were vacuum dried for about 1 hour at 40° C. and about 1 mm Hg abs. The adhering methanol, pX and mX were removed to afford 6.9 parts of an inclusion compound as white acicular crystals. A gas-chromatographic analysis of these crystals showed that they scarcely contained methanol, but consisted substantially only of pX and mX. The molar ratio of pX(pX+mX) was 0.61. From the results of the gas-chromatographic analysis, it was found that the inclusion ratio [(pX+mX)/MC molar ratio] was 0.89, and the degree of selection $\beta(pX/mX)$ was 27.

When the resulting inclusion compound was heated at 250° C. and about 100 mm Hg abs. to evaporate off the guest, 0.9 part of p-xylene having the same composition as set forth above $[pX/(pX+mX)=0.61]$ was obtained.

What we claim is:

1. A process for separating an isomer from a mixture containing isomers of a benzene derivative, which comprises contacting a meta-cyclophane of the formula

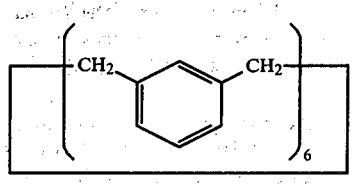

with a mixture containing isomers of a benzene derivative having substituents at 1- and 4-positions, or at 1-, 2- and 4-positions to thereby form an inclusion compound in which said benzene derivatives isomer is included in the meta-cyclophane, then separating the inclusion compound from the mixture, and thereafter separating the isomer from the inclusion compound.

2. A process of claim 1 wherein the benzene derivative is xylene, diethylbenzene, ethyltoluene, cresol, chlorotoluene, nitrotoluene, toluidine, ethylphenol, chloroethylbenzene, dichlorobenzene, trimethylbenzene, or triethylbenzene.

3. A process of claim 2 wherein the inclusion compound separated from the mixture is heated at a temperature of 90° to 400° C. to evaporate off the isomer included therein.

4. A process of claim 3 wherein the inclusion compound separated from the mixture is contacted with a solvent which can be more easily included by the meta-cyclophane than the isomers included therein to thereby replace the isomer by the solvent, then the resulting inclusion compound is which the solvent is included in the meta-cyclophane is separated by filtration, and then the isomer is separated from the filtrate, and then the isomer is separated from the filtrate by evaporation.

5. A process of claim 1 wherein the benzene derivative is mixed xylene containing p-xylene.

6. A process of claim 1 wherein the benzene derivative is a diethylbenzene isomer containing p-diethylbenzene.

7. A process of claim 1 wherein the benzene derivative is a halo-alkyl-benzene containing p-halo-alkyl-benzene.

8. A process of claim 1 wherein the benzene derivative is a tri-methylbenzene isomer.

9. A process for preparing an inclusion compound comprising contacting a meta-cyclophane represented by the formula

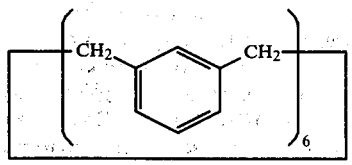

with at least one benzene derivative having substituents at 1- and 4-positions, or 1-, 2- and 4-positions as guest compounds.

10. A process of claim 9 which comprises mixing the meta-cyclophane with the mixture containing at least one said benzene derivative, heating the mixture to form a homogeneous liquid phase, and then cooling it.

11. The process of claim 9 wherein said benzene derivative is represented by the formula

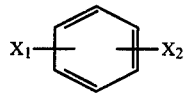

in which each $X_1$ and $X_2$, which may be the same or different, represents $-CH_3$, $-C_2H_5$ or $-C_3H_7$.

12. An inclusion compound comprising a meta-cyclphane represented by the formula

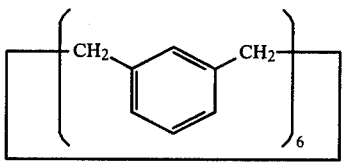

and at least one benzene derivative included therein, said benzene derivative having substituents at the 1- and 4-positions, or at the 1-, 2- and 4-position.

13. An inclusive compound of claim 12 wherein the benzene derivative is xylene, diethylbenzene, ethyltoluene, cresol, chlorotoluene, nitrotoluene, ethylphenol, chloroethylbenzene, dichlorobenzene, trimethylbenzene, toluidine, or triethylbenzene.

* * * * *